(12) United States Patent
Darby, II et al.

(10) Patent No.: US 12,167,774 B2
(45) Date of Patent: Dec. 17, 2024

(54) CONTOURED PEG INSOLE

(71) Applicant: DARCO INTERNATIONAL, INC., Huntington, WV (US)

(72) Inventors: H. Darrel Darby, II, Mount Pleasant, SC (US); Wu Zhang, Proctorville, OH (US); Thomas Dietrich, Raisting (DE)

(73) Assignee: DARCO INTERNATIONAL, INC., Huntington, WV (US)

( * ) Notice: Subject to any disclaimer, the term of this patent is extended or adjusted under 35 U.S.C. 154(b) by 11 days.

(21) Appl. No.: 15/861,929

(22) Filed: Jan. 4, 2018

(65) Prior Publication Data
US 2019/0200698 A1  Jul. 4, 2019

(51) Int. Cl.
| | |
|---|---|
| *A43B 7/14* | (2022.01) |
| *A43B 7/1415* | (2022.01) |
| *A43B 7/1455* | (2022.01) |
| *A43B 7/1463* | (2022.01) |
| *A43B 7/28* | (2006.01) |
| *A43B 13/12* | (2006.01) |
| *A43B 17/00* | (2006.01) |
| *A43B 17/16* | (2006.01) |

(52) U.S. Cl.
CPC .......... *A43B 7/1415* (2013.01); *A43B 7/1463* (2022.01); *A43B 7/147* (2013.01); *A43B 7/28* (2013.01); *A43B 13/12* (2013.01); *A43B 17/006* (2013.01); *A43B 17/16* (2013.01)

(58) Field of Classification Search
CPC ..... A43B 1/0009; A43B 7/1465; A43B 7/147; A43B 7/1485; A43B 17/006
See application file for complete search history.

(56) References Cited

U.S. PATENT DOCUMENTS

| | | | | |
|---|---|---|---|---|
| 4,179,826 | A | * 12/1979 | Davidson | A43B 21/32 36/129 |
| 5,067,256 | A | 11/1991 | Darby | |
| 5,154,682 | A | * 10/1992 | Kellerman | A43B 1/0072 36/178 |
| 5,329,705 | A | * 7/1994 | Grim | A43B 1/0009 36/110 |

(Continued)

FOREIGN PATENT DOCUMENTS

EP  0019673 A1  12/1980

OTHER PUBLICATIONS

International Search Report dated Dec. 4, 2018, issued by the International Searching Authority in application No. PCT/US2018/053674.

(Continued)

*Primary Examiner* — Sharon M Prange
(74) *Attorney, Agent, or Firm* — Sughrue Mion, PLLC

(57) ABSTRACT

A peg insole including an integrally molded unitary foam body covered. The foam body may be covered with a cover layer, such as a stretchable fabric, on a top surface of the foam body opposite the pegs. The foam body is includes a base layer with a plurality of pegs protruding therefrom. The foam body may include a contoured shaped to comfortably fit a patient's foot including, for example, a medial support portion, a lateral support portion, and a heel cup. The peg insole may be used, for example, in a medical shoe. Also provided is a method for forming the peg insole.

13 Claims, 12 Drawing Sheets
(6 of 12 Drawing Sheet(s) Filed in Color)

(56) References Cited

U.S. PATENT DOCUMENTS

| | | | |
|---|---|---|---|
| 5,551,173 A | 9/1996 | Chambers | |
| 5,768,803 A * | 6/1998 | Levy | A43B 7/1425 |
| | | | 36/140 |
| 5,778,565 A * | 7/1998 | Holt | A43B 1/0081 |
| | | | 36/101 |
| 6,301,805 B1 | 10/2001 | Howlett et al. | |
| 6,792,699 B2 * | 9/2004 | Long | A43B 1/0009 |
| | | | 36/154 |
| 7,231,728 B2 | 6/2007 | Darby | |
| 8,201,346 B2 | 6/2012 | Darby, II et al. | |
| 10,051,916 B1 * | 8/2018 | Short | A43B 17/006 |
| 2009/0320329 A1 | 12/2009 | Darby, II et al. | |
| 2011/0247235 A1 | 10/2011 | de Roode et al. | |
| 2012/0090198 A1 | 4/2012 | Stratten et al. | |
| 2015/0075030 A1 * | 3/2015 | Walborn | A43B 1/0009 |
| | | | 36/44 |
| 2015/0351949 A1 * | 12/2015 | Klutts | A61F 5/30 |
| | | | 602/5 |
| 2016/0353840 A1 | 12/2016 | Mason et al. | |
| 2017/0105482 A1 * | 4/2017 | Smaniotto | A43B 17/006 |

OTHER PUBLICATIONS

Written Opinion dated Dec. 4, 2018, issued by the International Searching Authority in application No. PCT/US2018/053674.
Communication dated Aug. 24, 2021, from the European Patent Office in application No. 18898065.0.
Search Report dated Aug. 6, 2021, from the European Patent Office in application No. 18898065.0.

* cited by examiner

CONTOURED PEG INSOLE

BACKGROUND

1. Field

Exemplary embodiments relate to peg insoles, particularly contoured peg insoles, which may be used in foot orthotics, such as in a medical shoe.

2. Description of the Related Art

In the field of foot orthotics, plaster castings are often considered the gold standard. However, plaster castings often require time consuming casting processes that may be uncomfortable to a patient and may result in increased treatment costs. As an alternative to plaster castings, peg insoles used with medical shoes have been employed to equalize pressure on a plantar surface of a patient's foot.

Conventional peg insoles for medical shoes are constructed of multiple layers of Ethyl Vinyl Acetate (EVA) or other suitable materials of varying densities. The multiple layers are laminated and then pegs are formed by, for example, die cutting the laminated insole. For example, as described in U.S. Pat. No. 8,201,346, the entirety of which is incorporated herein by reference, a layer of EVA may be laminated onto a layer of Plastizote (Plastizote is a medically inert, high density polyethylene closed cell foam having excellent memory and impact absorption properties). Thereafter, the laminate may be die cut to form die cut pegs and a top layer, to be contacted with a patient's foot, is then glued thereon. The top layer may be formed of, for example, Poron (Poron is an impact absorbing open cell cellular urethane foam product).

However, the conventional process described in U.S. Pat. No. 8,201,346 include multiple, distinct steps, which increases both cost and time of production. Additionally, since the top layer is glued to the pegs, the pegs can only be removed by either cutting through the pegs using a blade or other tool or forcefully ripping the pegs which may cause damage to the insole, particularly the top layer.

Other insoles such as those described in U.S. Pat. No. 7,231,728, the entirety of which is incorporated herein by reference, employ a multilayer structure over varying hardness wherein the layers may be rearranged in accordance with the needs of a patient. As such, production of such insoles require manufacturing several distinct layers and assembly thereof. Additionally, U.S. Pat. No. 7,231,728 describes creating an offload region by using a sharp instrument to remove a portion from one of the insole layers. However, such a process is only suitably performed by a healthcare professional and requires additional steps to rearrange the layers of the multilayer insole.

Exemplary embodiments overcome these shortcomings and solve the problems discussed above by simplifying the production process of the peg insole. As such, exemplary embodiments reduce manufacturing costs and offset the costs associated with more expensive memory foam products used in the exemplary embodiments. Further exemplary embodiments provide pegs that can be easily removed by a patient or practitioner without the use of blades or specialized tools and without damaging to the peg insole, namely the base layer of the foam body.

Additionally, conventional insoles for medical shoes, such as those described above, have a flat shape. As in U.S. Pat. No. 8,201,346, this is in part due to the difficulty involved in gluing a top layer onto a plurality of die cut pegs of varying heights. Similarly, as in U.S. Pat. No. 7,231,728, a contoured shape is difficult to achieve while employing a multilayer insole structure wherein the layers are to be rearranged during use. However, this flat shape increases pressure on a patient's foot, especially at the heel.

U.S. Pat. No. 5,067,256, the entirety of which is incorporated herein by reference, attempts to address this issue by providing an acupressure heel cup. However, the insole of U.S. Pat. No. 5,067,256 employs a non-compressible elastomer plastic or rubber, which does not provide the comfort and reduced pressure of a foam insole. The conventional configuration likewise does not allow the pegs to be easily removed to create an offload region further reducing pressure on an affected area of a patient's foot.

Exemplary embodiments include a contoured shape peg insole formed of a foam material. This configuration increases comfort to the patient and greatly reduces pressure while also providing selectively removable pegs.

BRIEF SUMMARY

In an exemplary embodiment, the peg insole includes an integrally formed unitary foam body including a base layer and a plurality of pegs protruding therefrom. The foam body may be covered with a cover layer, such as a stretchable fabric, on a top surface of the foam body opposite the pegs. The pegs may be separated from one another by a cutout portion formed during the molding process. The foam body may have a contoured shaped to comfortably fit a patient's foot including, for example, a medial support portion, a lateral support portion, and a heel cup. The peg insole may be used, for example, in a medical shoe.

BRIEF DESCRIPTION OF DRAWINGS

The application file contains at least one drawing executed in color. Copies of this application publication with the color drawings will be provided by the Office upon request and payment of the necessary fee.

These and/or other aspects will become apparent and more readily appreciated from the following description of exemplary embodiments, taken in conjunction with the accompanying drawings of which.

DETAILED DESCRIPTION

Figure 1:
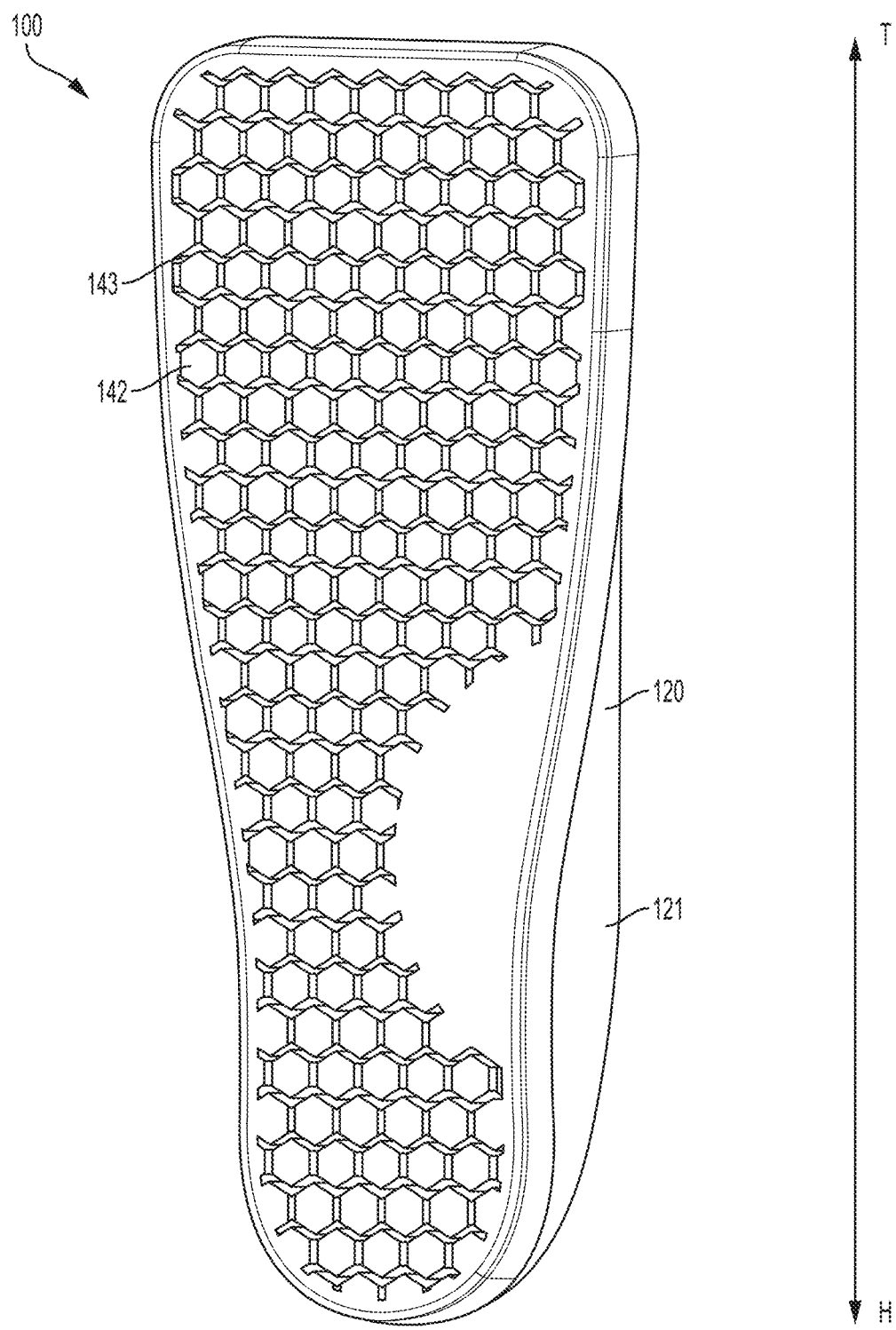
FIG. 1 is a perspective view of the peg insole without any offload region.

The present inventive concept may allow various kinds of change or modification and various changes in form, and specific exemplary embodiments will be illustrated in drawings and described in detail in the specification. However, it should be understood that the specific exemplary embodiments do not limit the present inventive concept to a specific disclosing form but include every modified, equivalent, or replaced one within the spirit and technical scope of the present inventive concept. In the following description, well-known functions or constructions are not described in detail since they would obscure the invention with unnecessary detail.

The terminology used in the application is used only to describe specific exemplary embodiments and does not have any intention to limit the present inventive concept. Although general terms as currently widely used as possible are selected as the terms used in the present inventive concept while taking functions in the present inventive concept into account, they may vary according to an intention of those of ordinary skill in the art, judicial precedents, or the appearance of new technology. In addition, in specific cases, terms intentionally selected by the applicant may be used, and in this case, the meaning of the terms will be disclosed in corresponding description of the invention. Accordingly, the terms used in the present inventive concept should be defined not by simple names of the terms but by the meaning of the terms and the content over the present inventive concept.

This description of the exemplary embodiments is intended to be read in connection with the accompanying drawings, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

In an exemplary embodiment, the peg insole 100 is formed of an integrally molded unitary foam body 140 including a base layer 141 with a plurality of pegs 142 protruding therefrom. Preferably, the pegs 142 are configured to be removable. The foam body 140 may be formed, for example, of a memory foam or other suitable materials. The memory foam may be an injection foam or an ether-based polyurethane foam, such as Ethyl Vinyl Acetate (EVA). In preferred embodiments, a density of the memory foam is 0.05-20 kg/cm$^3$, 0.10-10 kg/cm$^3$, 0.20-5.0 kg/cm$^3$, 0.25-2.0 kg/cm$^3$, 0.30-1.0 kg/cm$^3$, 0.35-0.50 kg/cm$^3$, or 0.40-0.42 kg/cm$^3$. In preferred embodiments, a rebound time or recovery time of the memory foam is 0.5-60 seconds, 1-30 seconds, 1.5-20 seconds, 1.75-15 seconds, 2.0-10 seconds, 2.5-7.5 seconds, or 3-5 seconds. Also, in preferred embodiments, the Shore C hardness of the memory foam is 10-50 degrees, 15-40 degrees, 20-35 degrees, 25-31 degrees, or 27-29 degrees.

In exemplary embodiments, the foam body 140 is integrally molded in the desired shape including at least a plurality of pegs 142 protruding from the base 141. Further, a cutout portion 143 separating the pegs 142 may be included in order to provide the peg insole 100 with additional flexibility. The height of the pegs 142 (that is, the depth of the cutout portion 143) is not particularly limited, and may be constant or varied. The height of the pegs 142 is set such that the cutout portion 143 does not extend through the entire thickness of the foam body 140. That is, the thickness of the base layer 141 (that is, the thickness shown by the arrows in Section C-C of FIG. 11) is greater than 0 mm. In preferred embodiments, the thickness of the base layer 141 is greater than 0 mm, preferably, from 0.1 to 20 mm, 0.5 to 15 mm, or 1.0 to 10 mm.

Figure 2:
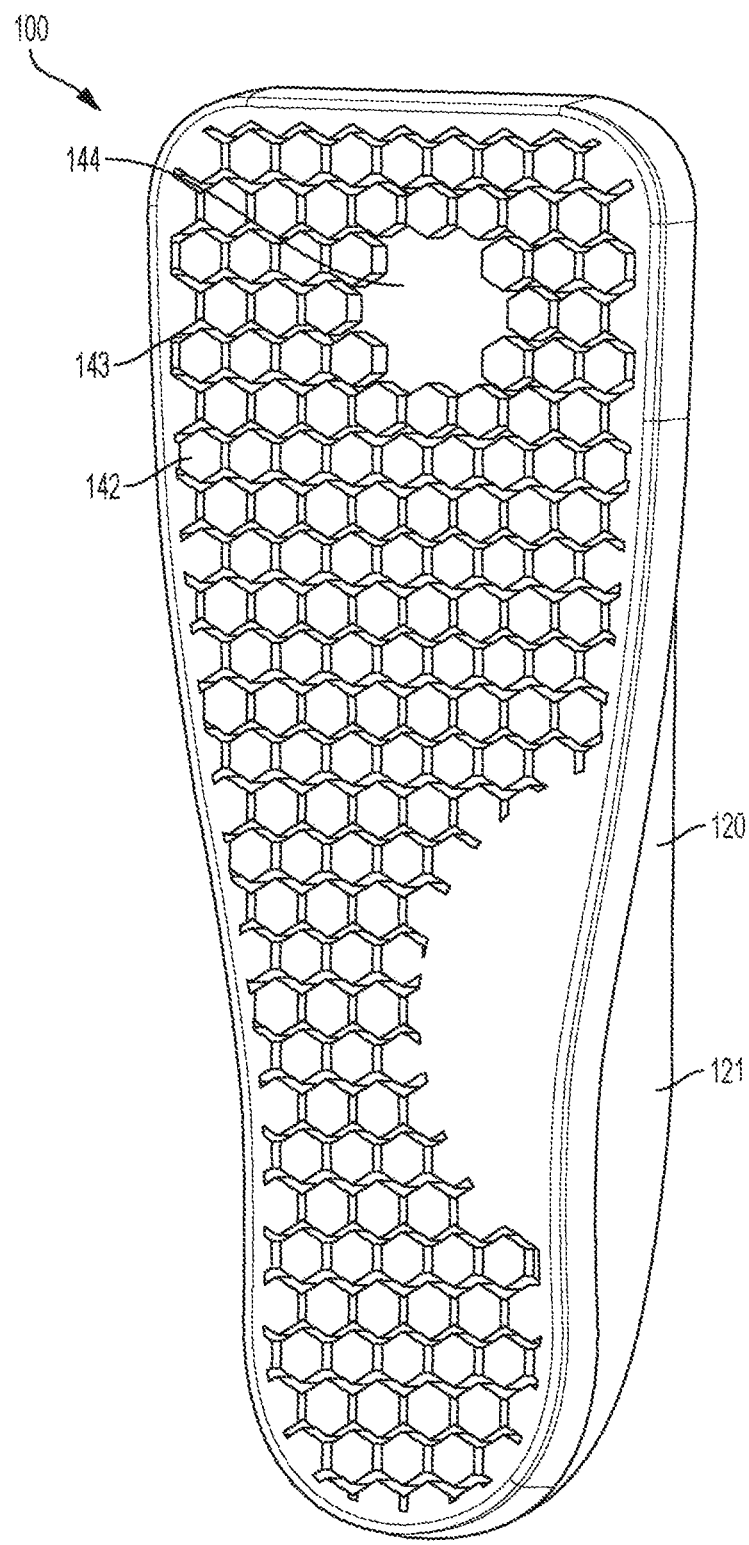
FIG. 2 is a perspective view of the peg insole including an offload region near a toe end of the peg insole.

The pegs 142 may be of any suitable shape, such as a hexagonal shape shown in FIGS. 1-2. In other embodiments, the shape of the pegs 142 may be elliptical or circular or polygonal, for example, triangular, rectangular, or square. Preferably, the area occupied by the cutout portion 143 is minimized in order to provide sufficient support to the patient by reducing void space. From this viewpoint, polygonal shaped pegs are preferable over elliptical or circular pegs. In preferred embodiments, the pegs 142 are evenly spaced from one another.

In exemplary embodiments, the pegs 142 are configured to be twisted off by hand and removed from the base layer 141 without damage to the foam body 140. Preferably, removal of the pegs 142 does not penetrate the base layer 141. As shown in FIG. 2, by selectively removing one or more pegs 142 from the peg insole 100, an offload region 144 may be formed in order to alleviate pressure in a selected area, for example, at the heel or at a metatarsal phalangeal joint. According to this embodiment, weight may be offloaded from a wound to a patient's foot in an area corresponding to the offload region 144. The offload region 144 preferably includes a remaining portion of the foam body 140 (i.e., the base layer 141) as well as any cover layer, not shown, that may be included in the peg insole 100, but does not include any pegs 142.

The depth of the offload region 144 (corresponding to the height of pegs 142 to be removed to form the offload region 144) is not particularly limited. In exemplary embodiments, the depth of the offload region 144 is configured such that, when the peg insole 100 is used in a medical shoe, a patient's foot in an area corresponding to the offload region 144 does not contact a midsole of the medical shoe. From this standpoint, the depth of the offload region 144 is preferably 1.0-25.0 mm, 3.0-20.0 mm, 5.0-15.0 mm, 7.0-13.0 mm, 8.0-12.0 mm, 9.0-11.0 mm, or 9.0-10.0 mm.

The width or diameter of each of the pegs 142 is not particularly limited and preferably is 1.0-25.0 mm, 5.0-20.0 mm, 7.5-15.0 mm, 8.0-12.0 mm, or 9.0-11.0 mm. If the pegs 142 are too large in terms of cross-sectional area, it becomes difficult to specify the offload region 144. If the pegs are too small, the number of pegs 142 required to form the offload region 144 increases, thereby making removal of the pegs 142 by a patient or healthcare professional more difficult and time consuming. Additionally, if the pegs 142 are too large, it may be difficult to remove the pegs 142 by hand due to increased force required and it may be difficult to avoid damage to the foam body 140 during removal of the pegs 142. Conversely, if the pegs are too small, the pegs 142 may be damaged and fall off during use of the peg insole 100. The distance between the centers of adjacent pegs 142 is not particularly limited and preferably is 1.0-25.0 mm, 5.0-20.0 mm, 7.5-15.0 mm, 8.0-12.0 mm, 9.0-11.0 mm, or about 10 mm.

In exemplary embodiments, the peg insole 100 may have a contoured shape including, for example, a side portion 120 having a medial support portion 121 for supporting the medial region of a patient's foot, including the arch of the foot, and a lateral support portion 122 for supporting the lateral region of a patient's foot. As shown in FIG. 4, the medial support portion 121 may have a height M that is greater than that of the height L of the lateral support portion 122. In other embodiments, the heights M and L may be equal to one another or the height L may be greater than that of the height M, depending on the needs of the patient. Additionally, in FIGS. 1-3, the medial support portion 121 is forward of the lateral support portion 122 in the toe direction T. In other embodiments, the medial support portion 121 may be aligned with or rearward of the lateral support portion 122 in the toe direction T. In one embodiment, the medial support portion 121 and later support portion 122 may be symmetrical in both location and height, such that the peg insole 100 may be used for either foot of the patient. In some embodiments, the entire peg insole 100 may have a symmetrical contoured shape. Further, the toe end T of the peg insole 100 may be formed with a squared off end for use in a medical shoe.

Figures 3A, 3B, 3C:
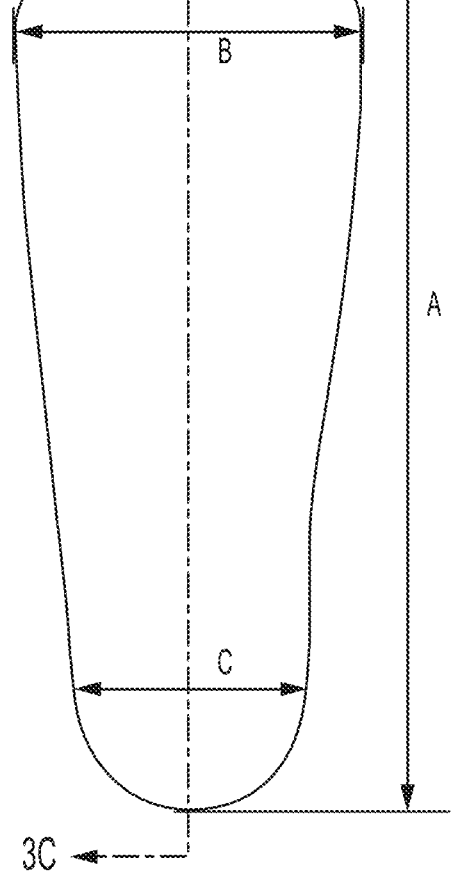
FIG. 3A is an anterior side view of the peg insole.
FIG. 3B is a top view of the peg insole.
FIG. 3C is a cross-section of the peg insole along the 3C-3C axis.
Figure 4:
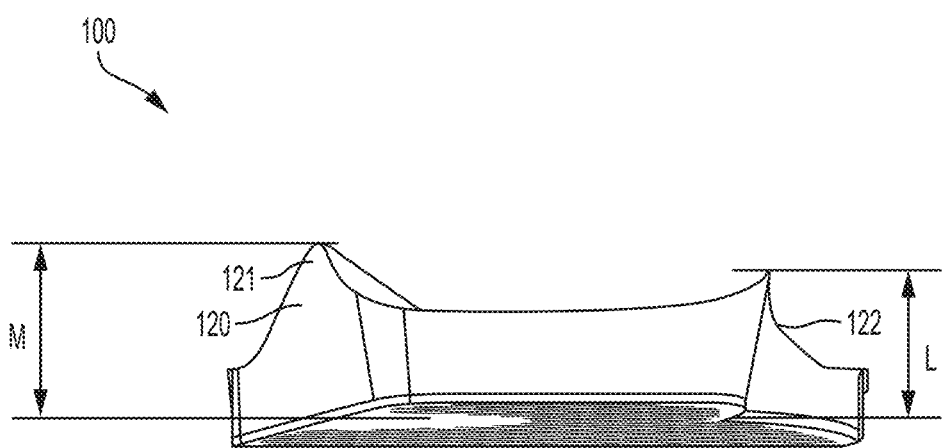
FIG. 4 is a rear view of the peg insole from a heel end thereof.
Figure 11:
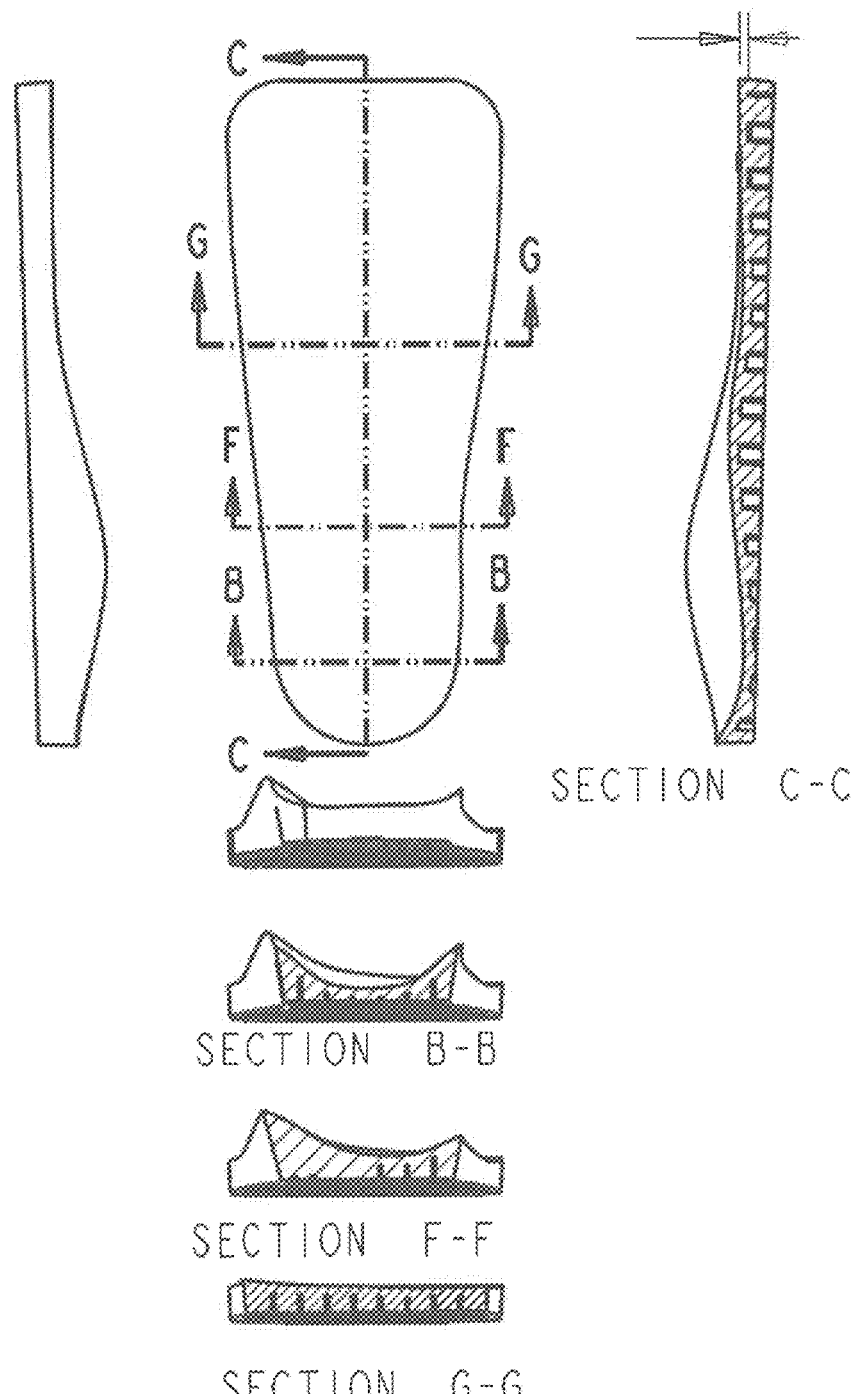
FIG. 11 shows cross-sections of the peg insole along various axes.
Figure 12:
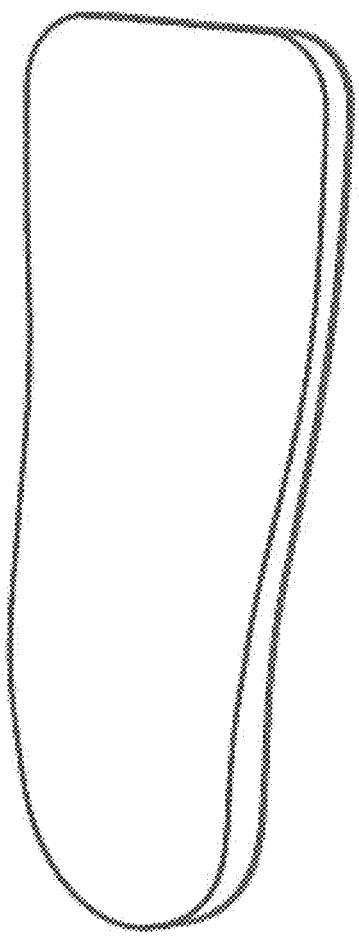
FIG. 12 is perspective view of the peg insole.

In an exemplary embodiment shown in FIGS. 3B-3C, foam body 140 includes a heel cup 131 that is depressed in order to comfortably accommodate a patient's heel and to reduce the pressure applied to the foot. As shown in the side view of FIG. 3C, the thickness at a center of the heel cup 131 is reduced as compared to a remainder of the peg insole 100. Preferably, the peg insole 100 tapers in thickness from horseshoe shaped heel end H toward the center of the heel cup 131. FIGS. 11 and 12 depict an exemplary embodiment of the peg insole having a contoured shape. Sections B-B and F-F in FIG. 11 demonstrate an exemplary configuration for the heel cup of the peg insole. FIG. 11 also shows an exemplary configuration for the lateral and medial support portions. This configuration can provide shock absorption, and reduces the edema, congestion, and inflammation of the soft tissues to reduce heel pain and discomfort for the patient.

In exemplary embodiments, the thickness of the foam body 140 in a region near the heel end H is less than the thickness of the foam body 140 in a region near the toe end T. For example, a ratio of a maximum thickness of the foam body a region near the toe end T to a minimum thickness of the foam body in a region near the heel end H may be 1-20, 3-15, 5-10, or 7-9. According to such a configuration, the peg insole 100 can provide increased offloading of pressure near the toe or forefoot of a patient.

In exemplary embodiments, the minimum thickness of the foam body 140 is 1.0-40.0 mm, 5.0-25.0 mm, 7.0-15.0 mm, 8.0-12.0 mm, or 9.0-10.0 mm. If the minimum thickness of the foam body 140 is too small, a patient's foot in the area of the minimum thickness may not be sufficiently supported by the peg insole 100 and the peg insole 100 may not be able to provide sufficient cushioning between the patient's foot and, for example, the midsole of a medical shoe.

Referring to FIG. 3B, a variety of insole dimensions are contemplated in order to accommodate a wide variety of foot shapes and sizes. The dimensions for A, B, and C of FIG. 3B may be, for example, as shown in the following Table 1. In exemplary embodiments, the values shown in Table 1 may acceptably vary by ±0.1 cm, ±0.25 cm, ±0.5 cm, ±0.75 cm, ±1.0 cm, ±2.0 cm, or ±5.0 cm. All dimensions in Table 1 are in centimeters (cm).

TABLE 1

| | Insole Dimensions | | |
|---|---|---|---|
| | A | B | C |
| Small | 26.00 | 9.25 | 6.25 |
| Medium | 27.00 | 10.25 | 7.00 |
| Large | 28.25 | 10.50 | 7.50 |
| X-Large | 30.50 | 11.00 | 7.50 |
| XX-Large | 32.00 | 11.25 | 7.75 |

The peg insole 100 may include a cover layer, not shown, laminated to an upper surface of the foam body 140 opposite of the pegs 142. The cover layer may be made of, for example, a stretchable fabric or other suitable materials. When included in the peg insole 100, the cover layer contacts the patient's foot and provides additional cushioning and comfort. Additionally, the cover layer may be formed of a breathable fabric in order to keep the patient's foot cool and dry.

In an exemplary method of producing the peg insole 100, the unitary foam body 140 is integrally molded of a foam material to provide the desired shape including at least a plurality of pegs 142 protruding from the base layer 141. The pegs 142 may be separated by a cutout portion 143 formed during the molding process. The molding may be done, for example, by injection molding or by any other suitable method.

In some embodiments, the molded foam body 140 may be cured to provide a cured molded foam body 140. However, the peg insole 100 may be formed without any curing process, thereby further reducing production time and associated costs. In embodiments including the cover layer, not shown, the cover layer may be applied to the molded foam body 140 on an upper surface opposite of the pegs 142. The cover layer may be applied to the molded foam body 140 using an adhesive and then laminated onto the foam body 140 during a curing process. Alternatively, the cover layer may be applied and laminated to the foam body 140 without curing or after the foam body 140 has been cured. In another embodiment, the cover layer, optionally including an adhesive on one side thereof, may be placed into the mold prior to injection molding of the foam body 140. In such an embodiment, the cover layer is laminated onto the foam body 140 during injection molding. Once the cover layer has been laminated onto the foam body 140, excess portions of the cover layer may be removed by, for example, using a trim die.

In exemplary embodiments, the method may further include selectively removing one or more pegs 142 to form an offload region 144. In exemplary embodiments, the pegs 142 may be removed by hand by a healthcare professional or a patient. Preferably, removal of the pegs 142 does not penetrate the base layer 141, and when the cover layer, not shown, is employed, removal of the pegs 142 does not expose a lower surface of the cover layer.

According to the embodiments described above, by using a memory foam material along with the contoured shape, the peg insole 100 provides increased contact with a patient's foot thereby providing reduced pressure on a patient's foot. According to preferred embodiments, since the patient's foot sinks into the memory foam, not only is comfort improved but contact between the insole and a plantar surface of the patient's foot may be increased by 40% or more as compared with conventional insoles and pressure on the foot may be decreased by 20-30%. Further, by including the memory foam material in the peg insole 100 having a contoured shape, especially having heel cup 131, shifting of the patient's foot (i.e., shear force) may be decreased as the material and shape provide a so call "lockdown function." Specifically, the "lockdown function" is, at least in part, due to the contoured shape providing increased contact area (i.e., increased area of contact between the insole 100 and a patient's foot) at positions perpendicular to a shear force, for instance, at lateral surfaces of the foot. Also, the contoured shape provides increased contact area in the arch of a patient's foot, which further contributes to the "lockdown function." This can reduce friction on, and irritation to, the soft tissue of the patient's foot during use of a medical shoe including the peg insole 100.

Example 1

Figure 5A:
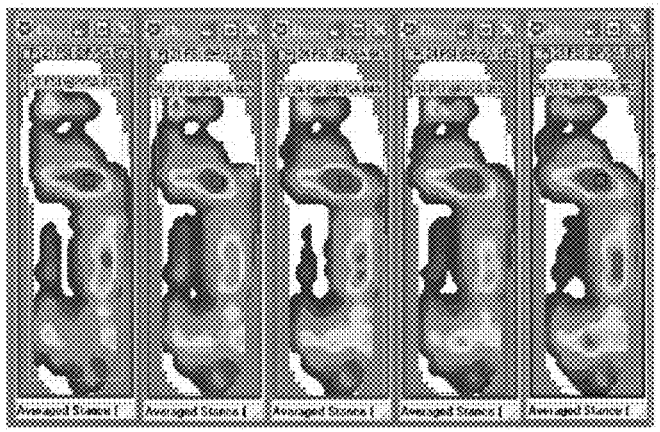
FIG. 5A is pressure maps for the peg insole used in a medical shoe corresponding to Example 1.
Figure 5B:
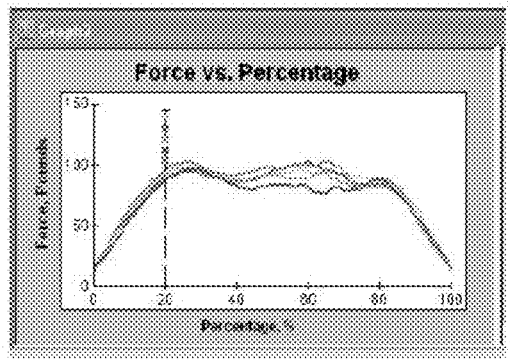
FIG. 5B is a graph of force versus percentage for the peg insole used in a medical shoe in Example 1.

A contoured peg insole formed of polyurethane memory foam (density of 0.40-0.42 kg/cm$^3$; Shore C hardness of 28 degrees±3 degrees; tear resistance strength of 2.5-3.5 kg/cm$^2$; tensile strength of 2.5-3.5 kg/cm$^2$, rebound time of 3 to 5 seconds) was inserted into the Dual Density Med-Surg™ (available from Darco International, Inc.) and a pressure test was conducted as follows. Pressure measurements were taken for a user wearing the Dual Density Med-Surg™ over five paces using the F-Scan System (available from Tekscan, Inc.). The resulting pressure maps for the five paces are shown in FIG. 5A. The results are also plotted in FIG. 5B as force versus percentage of each pace.

Comparative Example 1

Figure 6A:
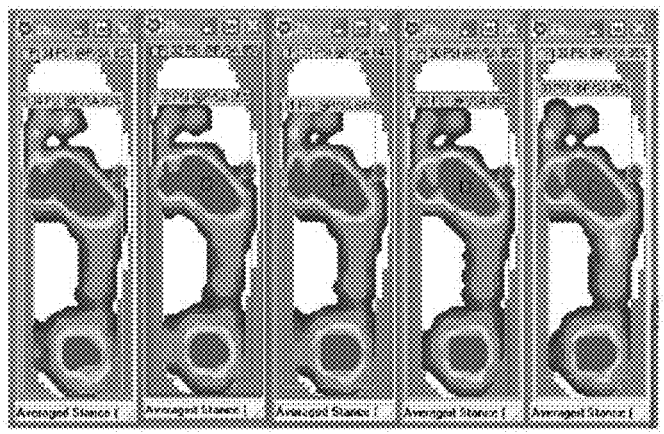
FIG. 6A is pressure maps for a conventional insole when used in a medical shoe corresponding to Comparative Example 1.
Figure 6B:
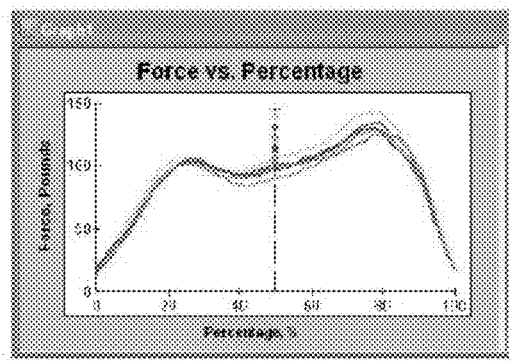
FIG. 6B is a graph of force versus percentage for the conventional insole used in a medical shoe in Comparative Example 1.

The procedures of Example 1 were repeated except that a conventional flat EVA insole was used in place of the contoured memory foam peg insole. The results are shown in the pressure map in FIG. 6A and in the force versus percentage plot in 6B.

Figure 7:
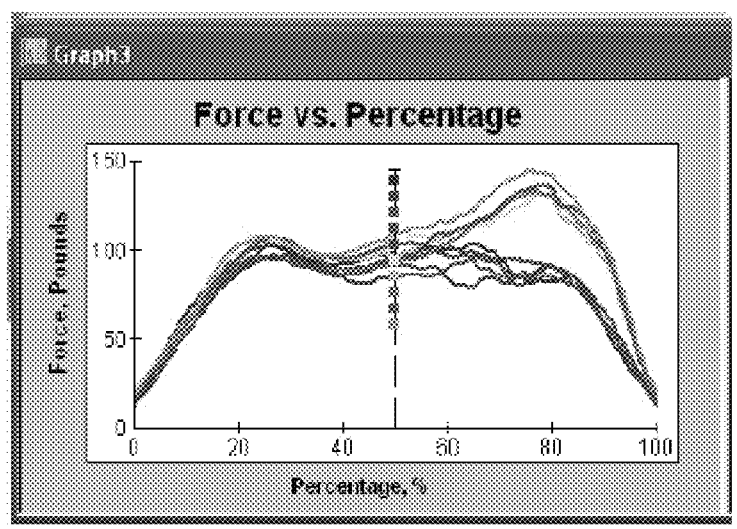
FIG. 7 is an overlay of the graphs from FIG. 5B and FIG. 6B.

As evident from FIG. 7, which shows the results of Example 1 compared to the results of Comparative Example 1, the contoured peg insole of Example 1 was able to provide a 20-30% pressure reduction as compared with the conventional insole of Comparative Example 1.

Example 2

Figure 8A:
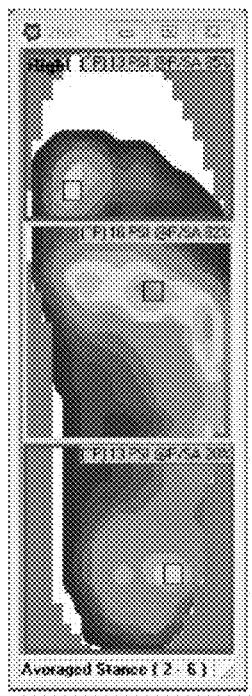
FIG. 8A is a pressure map showing the average results of Example 2.
Figure 8B:
FIG. 8B shows a toe portion of the insole used in Example 2.

The procedures of Example 1 were repeated with a new user wearing the Dual Density Med-Surg™ including the contoured peg insole shown in FIG. 8B. The average pressure map of Example 2 is shown in FIG. 8A. The results of Example 2 are summarized in Tables 2 and 3 below.

Example 3

Figure 9A:
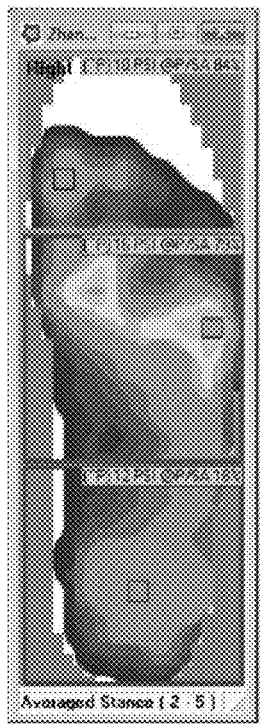
FIG. 9A is a pressure map showing the average results of Example 3.
Figure 9B:
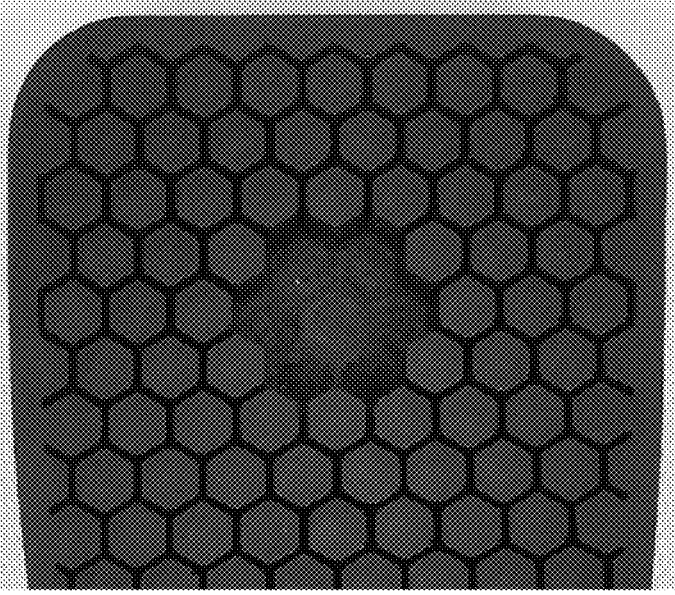
FIG. 9B shows a toe portion of the insole used in Example 3 including an offload region.

The procedures of Example 2 were repeated except that an offload region was formed in the contoured peg insole in an area near the third metatarsal head, as shown in FIG. 9B. The average pressure map of Example 3 is shown in FIG. 9A. The results of Example 3 are summarized in Tables 2 and 3 below.

Comparative Example 2

Figure 10A:
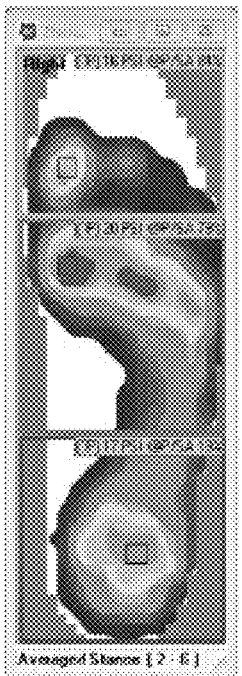
FIG. 10A is a pressure map showing the average results of Comparative Example 2.
Figure 10B:
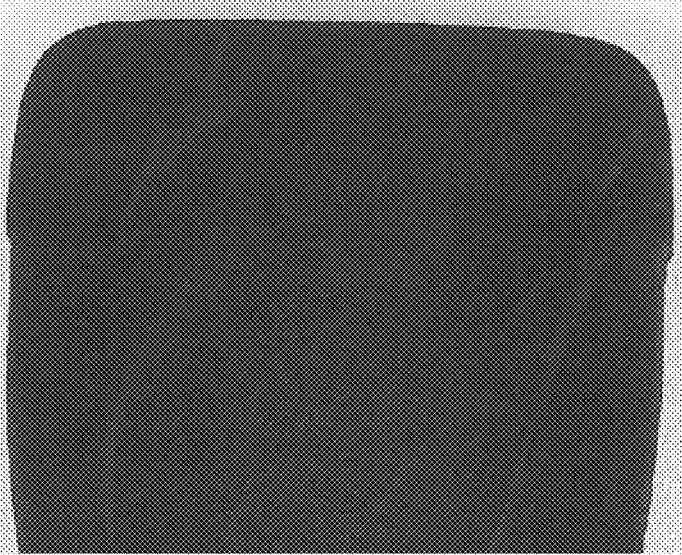
FIG. 10B shows a toe portion of the insole used in Comparative Example 2.

The procedures of Example 2 were repeated except that a conventional flat EVA insole was used in place of the contoured memory foam peg insole. A toe region of the insole used it shown in FIG. 10B, and the average pressure map of Comparative Example 2 is shown in FIG. 10A. The results of Comparative Example 2 are summarized in Tables 2 and 3 below.

TABLE 2

| | | Pace 1 | Pace 2 | Pace 3 | Pace 4 | Pace 5 | Average |
|---|---|---|---|---|---|---|---|
| Comparative Example 2 | Third meta-head pressure (PSI) | 20 | 19 | 20 | 19 | 20 | 19.6 |
| | Toe pressure (PSI) | 16 | 13 | 12 | 14 | 12 | 13.4 |
| | Forefoot pressure (PSI) | 20 | 19 | 20 | 19 | 20 | 19.6 |
| | Heel pressure (PSI) | 17 | 16 | 17 | 17 | 17 | 16.8 |
| Example 2 | Third meta-head pressure (PSI) | 17 | 16 | 16 | 17 | 17 | 16.6 |
| | Toe pressure (PSI) | 13 | 13 | 11 | 12 | 13 | 12.4 |
| | Forefoot pressure (PSI) | 17 | 16 | 17 | 17 | 17 | 16.8 |
| | Heel pressure (PSI) | 13 | 13 | 14 | 15 | 14 | 13.8 |
| Example 3 | Third meta-head pressure (PSI) | 5 | 5 | 4 | 5 | 4 | 4.6 |
| | Toe pressure (PSI) | 11 | 10 | 11 | 10 | 10 | 10.4 |
| | Forefoot pressure (PSI) | 16 | 16 | 16 | 17 | 17 | 16.4 |
| | Heel pressure (PSI) | 10 | 12 | 13 | 13 | 13 | 12.2 |

TABLE 3

| | Example 2 vs. Comparative Example 2 | Example 3 vs. Comparative Example 2 | vs. Example 2 |
|---|---|---|---|
| Offloading at third metatarsal head | 15.31% | 76.53% | 72.29% |
| Offloading in toe | 7.46% | 22.39% | 16.13% |
| Offloading in forefoot | 14.29% | 16.33% | 2.38% |
| Offloading in heel | 17.86% | 27.38% | 11.59% |

In Table 3, the percentage of offloading was calculated as a percentage decrease in pressure of Example 2 (contoured memory foam peg insole) as compared with Comparative Example 2 (standard insole), and of Example 3 (contoured memory foam peg insole with offload region) as compared with Comparative Example 2 (standard insole) and Example 2 (contoured memory foam peg insole). The toe, forefoot, and heel correspond to the top, middle, and bottom boxed areas, respectively, shown in FIGS. 8A, 9A, and 10A.

From Table 3 above, it can be seen that the contoured peg insole formed of memory foam used in Example 2 provided significant offloading in all areas of the foot as compared with the conventional insole used in Comparative Example 2. Further offloading was achieved in all areas of the foot in Example 3, wherein an offloading region was formed near the third metatarsal head.

While the exemplary embodiments have been particularly shown and described, it will be understood by those of ordinary skill in the art that various changes in form and details may be made therein without departing from the spirit and scope of the inventive concept as defined by the appended claims.

The invention claimed is:

1. A peg insole comprising:
an integrally molded unitary body; wherein
the body consists of a base layer and a plurality of pegs protruding from the base layer,
the base layer is contoured at a side of the base layer facing opposite a direction in which the plurality of pegs are protruding from the base layer,
the side of the base layer facing opposite from the pegs is exposed,
a contoured portion of the base layer is contoured in the direction away from the pegs and comprises a heel cup,
in a longitudinal direction of the body, the heel cup is arranged at a first side of the body opposite to a second side of the body,
in a direction in which the pegs are protruded from the base layer, at least one of the pegs at the first side of the body is shorter than another one of the pegs at the second side, and
a height is varied such that the height is greater at a medial portion of the heel cup between the first side and the second side than at an end of the body at the first side.

2. The peg insole of claim 1, wherein the peg insole is contoured including raised medial and lateral side portions.

3. The peg insole of claim 1, wherein the pegs are configured to be selectively removable without penetrating through the base layer.

4. The peg insole of claim 1, wherein a thickness of the base layer is from 0.5-20 mm.

5. The peg insole of claim 1, wherein the pegs are spaced from one another on all lateral sides thereof.

6. A medical shoe comprising the peg insole according to claim 1.

7. The peg insole of claim 1, wherein the pegs are hexagonal.

8. The peg insole of claim 1, wherein the body comprises a foam material that comprises a density of 0.05-20 kg/cm$^3$.

9. The peg insole of claim 1, wherein the pegs comprise a first peg and a second peg, and
wherein the first peg is extended a greater distance through the body than is the second peg.

10. The peg insole of claim 9, wherein a face of the first peg and a face of the second peg together form a flat surface facing away from an upper side of the body.

11. The peg insole of claim 1,
wherein the pegs are further configured to be removed from the base layer by a tool.

12. A peg insole comprising:
a unitarily molded unitary body; wherein
the body includes a base layer and a plurality of pegs protruding from the base layer,
the base layer is contoured at a side of the base layer facing opposite a direction in which the plurality of pegs are protruding from the base layer,
the side of the base layer facing opposite from the pegs is exposed, and
wherein a contoured portion of the base layer is contoured in the direction away from the pegs and comprises a heel cup,
wherein, in a longitudinal direction of the body, the heel cup is arranged at a first side of the body opposite to a second side of the body,
wherein, in a direction in which the pegs are protruded from the base layer, at least one of the pegs at the first side of the body is shorter than another one of the pegs at the second side, and
wherein a height is varied such that the height is greater at a medial portion of the heel cup between the first side and the second side than at an end of the body at the first side.

13. A peg insole comprising:
an integrally molded unitary body,
wherein the body consists of a base layer and a plurality of pegs protruding from the base layer,
wherein the base layer is contoured,
wherein a contoured portion of the base layer is contoured in the direction away from the pegs and comprises a heel cup,
wherein, in a longitudinal direction of the body, the heel cup is arranged at a first side of the body opposite to a second side of the body, and
wherein, in a direction in which the pegs are protruded from the base layer, at least one of the pegs at the first side of the body is shorter than another one of the pegs at the second side.

* * * * *